(12) United States Patent
Evans et al.

(10) Patent No.: US 10,420,586 B2
(45) Date of Patent: *Sep. 24, 2019

(54) OBTURATOR TIP WITH INSUFFLATION PATHWAY

(71) Applicant: Covidien LP, Mansfield, MA (US)

(72) Inventors: Christopher Kelly Evans, Southington, CT (US); Gregory Fischvogt, Denver, CO (US)

(73) Assignee: Covidien LP, Mansfield, MA (US)

( * ) Notice: Subject to any disclaimer, the term of this patent is extended or adjusted under 35 U.S.C. 154(b) by 294 days.

This patent is subject to a terminal disclaimer.

(21) Appl. No.: 15/609,740

(22) Filed: May 31, 2017

(65) Prior Publication Data

US 2017/0258494 A1 Sep. 14, 2017

Related U.S. Application Data

(63) Continuation of application No. 13/905,363, filed on May 30, 2013, now Pat. No. 9,693,802.

(Continued)

(51) Int. Cl.
*A61B 17/34* (2006.01)

(52) U.S. Cl.
CPC .. *A61B 17/3474* (2013.01); *A61B 2017/3454* (2013.01)

(58) Field of Classification Search
CPC ............ A61B 17/3474; A61B 17/3417; A61B 17/3478; A61B 2017/3454;

(Continued)

(56) References Cited

U.S. PATENT DOCUMENTS 3,459,189 A * 8/1969 Alley ................. A61B 17/3415
604/166.01
4,666,438 A * 5/1987 Raulerson ............. A61M 5/158
604/166.01

(Continued)

FOREIGN PATENT DOCUMENTS

JP          17-005461          5/1942

OTHER PUBLICATIONS

Japanese Notice of Allowance issued in corresponding Japanese Application No. 2013-118626 dated Nov. 16, 2017.

(Continued)

*Primary Examiner* — Andrew M Gilbert (57) ABSTRACT

A surgical access apparatus including a cannula defining an internal lumen, the cannula having a connection for receiving insufflation fluid. The apparatus also includes an obturator assembly, the obturator assembly configured to be inserted through a cannula so as to define an interstitial space between the cannula and the obturator assembly. The interstitial space is in fluid communication with the cannula connection so as to convey the insufflation fluid. The obturator assembly includes an obturator shaft having a hollow interior and a tip member at a distal end of the obturator shaft. The tip member is configured to penetrate and/or dissect through tissue. The tip member has an outer surface that defines a channel, the channel being in fluid communication with the interstitial space to as to convey the insufflation fluid from a proximal end of the tip member to a distal end of the tip member.

17 Claims, 8 Drawing Sheets

Related U.S. Application Data (60) Provisional application No. 61/656,126, filed on Jun. 6, 2012.

(58) Field of Classification Search
CPC ... A61B 2017/34158; A61B 2017/349; A61M 25/0102; A61M 25/06; A61M 25/0606; A61M 25/065; A61M 5/158; A61M 13/00
See application file for complete search history.

(56) References Cited

U.S. PATENT DOCUMENTS

| | | | |
|---|---|---|---|
| 5,271,380 A | 12/1993 | Riek et al. | |
| 5,308,336 A | 5/1994 | Hart et al. | |
| 5,314,417 A | 5/1994 | Stephens et al. | |
| 5,334,150 A | 8/1994 | Kaali | |
| 5,352,206 A * | 10/1994 | Cushieri | A61B 5/03 604/158 |
| 5,364,372 A * | 11/1994 | Danks | A61B 17/3462 604/162 |
| 5,380,291 A | 1/1995 | Kaali | |
| 5,385,553 A | 1/1995 | Hart et al. | |
| 5,431,151 A | 7/1995 | Riek et al. | |
| 5,551,947 A | 9/1996 | Kaali | |
| 5,569,291 A | 10/1996 | Privitera et al. | |
| 5,569,292 A | 10/1996 | Scwemberger et al. | |
| 5,591,186 A * | 1/1997 | Wurster | A61B 17/3417 604/164.12 |
| 5,591,192 A | 1/1997 | Privitera et al. | |
| 5,609,562 A | 3/1997 | Kaali | |
| 5,685,820 A | 11/1997 | Riek et al. | |
| 5,709,671 A | 1/1998 | Stephens et al. | |
| 5,720,761 A * | 2/1998 | Kaali | A61B 1/00087 600/101 |
| 5,776,112 A | 7/1998 | Stephens et al. | |
| 5,843,039 A * | 12/1998 | Klemm | A61B 17/3417 604/164.01 |
| 5,853,392 A * | 12/1998 | Dennis | A61B 17/3494 604/164.01 |
| 6,007,481 A | 12/1999 | Riek et al. | |
| 6,007,544 A * | 12/1999 | Kim | A61B 17/320016 606/108 |
| 6,478,806 B2 | 11/2002 | McFarlane | |
| 6,497,687 B1 * | 12/2002 | Blanco | A61B 17/3494 604/274 |
| 6,685,630 B2 * | 2/2004 | Sauer | A61B 17/34 600/104 |
| 6,830,578 B2 | 12/2004 | O'Heeron et al. | |
| 6,835,201 B2 | 12/2004 | O'Heeron et al. | |
| 6,884,253 B1 | 4/2005 | McFarlane | |
| 6,960,164 B2 | 11/2005 | O'Heeron | |
| 7,320,694 B2 | 1/2008 | O'Heeron | |
| 7,470,230 B2 * | 12/2008 | Smith | A61B 17/34 600/184 |
| 7,686,823 B2 | 3/2010 | Pingleton et al. | |
| 7,758,603 B2 | 7/2010 | Taylor et al. | |
| 7,947,058 B2 | 5/2011 | Kahle et al. | |
| 7,981,089 B2 * | 7/2011 | Weilbacher | A61J 1/2096 604/243 |
| 8,012,128 B2 | 9/2011 | Franer et al. | |
| 8,152,828 B2 | 4/2012 | Taylor et al. | |
| 8,267,952 B2 | 9/2012 | Kahle et al. | |
| 8,317,815 B2 * | 11/2012 | Mastri | A61B 17/3417 606/185 |
| 8,574,238 B2 * | 11/2013 | Zannis | A61B 17/0401 606/99 |
| 8,790,308 B2 * | 7/2014 | Melvin | A61B 17/34 604/164.01 |
| 8,979,883 B2 | 3/2015 | Smith | |
| 9,168,059 B2 * | 10/2015 | Melvin | A61B 17/34 |
| 9,693,802 B2 * | 7/2017 | Evans | A61B 17/3474 |
| 2004/0230218 A1 * | 11/2004 | Criscuolo | A61B 17/3421 606/190 |
| 2005/0107816 A1 * | 5/2005 | Pingleton | A61B 17/3417 606/185 |
| 2005/0288622 A1 * | 12/2005 | Albrecht | A61B 17/3417 604/23 |
| 2006/0224174 A1 | 10/2006 | Smith et al. | |
| 2007/0203456 A1 * | 8/2007 | McClellan | A61B 17/3417 604/168.01 |
| 2008/0300617 A1 | 12/2008 | Smith | |
| 2009/0318868 A1 * | 12/2009 | Racenet | A61B 17/34 604/167.01 |
| 2010/0081988 A1 * | 4/2010 | Kahle | A61B 17/3474 604/26 |
| 2010/0324488 A1 * | 12/2010 | Smith | A61B 17/3417 604/164.11 |
| 2011/0087169 A1 * | 4/2011 | Parihar | A61B 17/34 604/167.03 |
| 2016/0000462 A1 * | 1/2016 | Pajunk | A61B 17/3417 604/26 |
| 2016/0045224 A1 * | 2/2016 | Hendershot, III | A61B 17/3474 604/26 |

OTHER PUBLICATIONS

Australian Examination Report issued in corresponding Australian Application No. 2017248448 dated Aug. 23, 2018.
Partial European Search Report for EP Application Serial No. 13 17 0927, dated Aug. 7, 2014, 6 pages.
Chinese Office Action dated Jun. 1, 2016 in corresponding Chinese Patent Application No. 201310224398.2, together with English translation, 19 pages.
Australian Examination Report dated Nov. 18, 2016 in corresponding Australian Patent Application No. 2013206180, 3 pages.
Chinese Office Action dated Feb. 3, 2017 in corresponding Chinese Patent Application No. 201310224398.2 with English translation, 19 pages.
Japanese Office Action dated Mar. 22, 2017 in corresponding Japanese Application No. 2013-118626, 12 pages.
Chinese Office Action dated Aug. 1, 2017 in corresponding Chinese Patent Application No. 201310224398.2, together with English translation, 9 pages.
Canadian Office Action issued in Application No. 2,817,410 dated Feb. 8, 2019, 4 pages.

\* cited by examiner

OBTURATOR TIP WITH INSUFFLATION PATHWAY

CROSS-REFERENCE TO RELATED APPLICATIONS

The present application is a Continuation of U.S. patent application Ser. No. 13/905,363, filed May 30, 2013, now U.S. Pat. No. 9,693,802. This application also claims priority to, and the benefit of, U.S. Provisional Patent Application Ser. No. 61/656,126, filed Jun. 6, 2012, entitled "OBTURATOR TIP WITH INSUFFLATION PATHWAY," the entire contents of each of which are incorporated herein by reference.

BACKGROUND

Technical Field

The present disclosure relates to a surgical access assembly including an obturator and a cannula. More particularly, the present disclosure relates to an obturator including a tip member with an outer surface having at least one channel for transmitting fluids therealong.

Background of Related Art

Minimally invasive procedures are continually increasing in number and variation. Forming a relatively small diameter, temporary pathway to the target site is a key feature of most minimally invasive surgical procedures. The most common method of providing such a pathway is by inserting an access assembly through the skin. Common access assemblies generally include a cannula configured to accommodate a trocar for penetrating tissue, and an obturator for dilating and creating a pathway through tissue. Obturators may be blunt members that are inserted through the cannula to tunnel a path through tissue and subsequently to a selected surgical site.

Minimally invasive procedures often supply insufflation fluids, e.g., carbon dioxide, to a body cavity underlying a layer of tissue such that the layer of tissue lifts away from underlying tissue or organ structures to create a larger working space. To this end, a source of insufflation fluid may be coupled to the cannula such that insufflation fluids flow distally into a body cavity. In many procedures, it is desirable to insufflate the body cavity of a patient while the obturator is inserted through the cannula. In such an arrangement, insufflation fluids may be introduced through an interior portion of the obturator, and exit through an opening in a distal portion or tip of the obturator within the working space. Such an arrangement typically incorporates an additional source of insufflation fluid coupled with the obturator, as well as sealing member within the obturator to inhibit the proximal migration of insufflation fluids through the obturator.

SUMMARY

The present invention, in accordance with various embodiments thereof, is directed to a surgical access apparatus, comprising: a cannula including a housing and a cannula shaft, the cannula shaft defining an internal lumen; and an obturator insertable through the internal lumen of the cannula, the obturator including: an obturator shaft having a proximal end and a distal end, and defining a longitudinal axis; and a tip member at the distal end of the obturator shaft, the tip member configured to be inserted through tissue and having an outer surface, the outer surface defining a channel for insufflation fluid.

The obturator may be configured to receive within an interior space thereof an endoscope, and at least a portion of the tip member, or even the entire tip member, may permit light to be transmitted therethrough so as to provide for an optical obturator. Advantageously, the channel is not in fluid communication with an interior of the obturator so as to avoid the need for a seal between the obturator and the endoscope. In an embodiment, a distal most end of the channel is at or adjacent to a distalmost end of the tip member so as to enable insufflation fluids to begin to be introduced into the body cavity almost immediately upon the distal tip of the tip member penetrating through the wall of the body cavity, reducings the likelihood that an injury to underlying anatomical structures will occur and further improving patient safety.

The outer surface of the tip member may define a plurality of channels. When the obturator shaft is disposed in the lumen of the cannula shaft, an annular space may be defined between the obturator shaft and the cannula shaft. A portion of the channel may be in fluid communication with the annular space. In addition, when the obturator is inserted in the lumen of the cannula shaft, at least a portion of the channel may extend distally of the cannula shaft. Still further, at least one seal member may be disposed in the cannula. Such a seal may be configured to form a fluid-tight seal with the obturator inserted therethrough. The cannula may be configured to be coupled to a source of fluid. The channel may be defined by an open proximal end, an open distal end, and a pair of opposed walls extending therebetween.

In other embodiments, the present invention may be directed to an obturator assembly that is configured to be inserted through a cannula. The obturator assembly may comprise an obturator shaft having a tip member at a distal end of the obturator shaft, the tip member configured to at least one of penetrate and dissect through tissue, the tip member having an outer surface that defines a channel, the channel configured to convey insufflation fluid from a proximal end of the tip member to a distal end of the tip member.

The obturator may have a hollow interior, and the hollow interior of the obturator may be configured to receive an endoscope. At least a portion of the tip member may permit light to be transmitted therethrough, and in various embodiments, the entire tip member may be light transmissible so as to provide an optical obturator.

In other embodiments, the present invention may be directed to a surgical access apparatus, comprising a cannula including a housing and a cannula shaft, the cannula shaft defining an internal lumen, the cannula having a connection for receiving insufflation fluid; and an obturator assembly, the obturator assembly configured to be inserted through a cannula so as to define an interstitial space between the cannula and the obturator assembly, the interstitial space being in fluid communication with the cannula connection so as to convey the insufflation fluid received by the connection, the obturator assembly including an obturator shaft having a hollow interior and a tip member at a distal end of the obturator shaft, the tip member configured to at least one of penetrate and dissect through tissue, the tip member having an outer surface that defines a channel, the channel being in fluid communication with the interstitial space to as to convey the insufflation fluid from a proximal end of the tip member to a distal end of the tip member, the channel not being in fluid communication with the interior of the obturator. In various embodiments, at least a portion of the tip member may permit light to be transmitted therethrough. Advantageously, the entire tip member may be fabricated from a material that permits light to be transmitted therethrough, thereby providing an optical obturator for use with the endoscope.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Embodiments of the presently disclosed surgical access apparatus for use in minimally invasive procedures are described in detail with reference to the drawings, in which like reference numerals designate identical or corresponding elements in each of the several views. As used herein, the term "distal" refers to that portion of the apparatus which is farther from the operator while the term "proximal" refers to that portion of the apparatus which is closer to the operator. The presently disclosed surgical access apparatus is usable in an opening through a patient's tissue, such as an incision or a naturally-occurring orifice (e.g., mouth, anus, or vagina).

Figure 8:
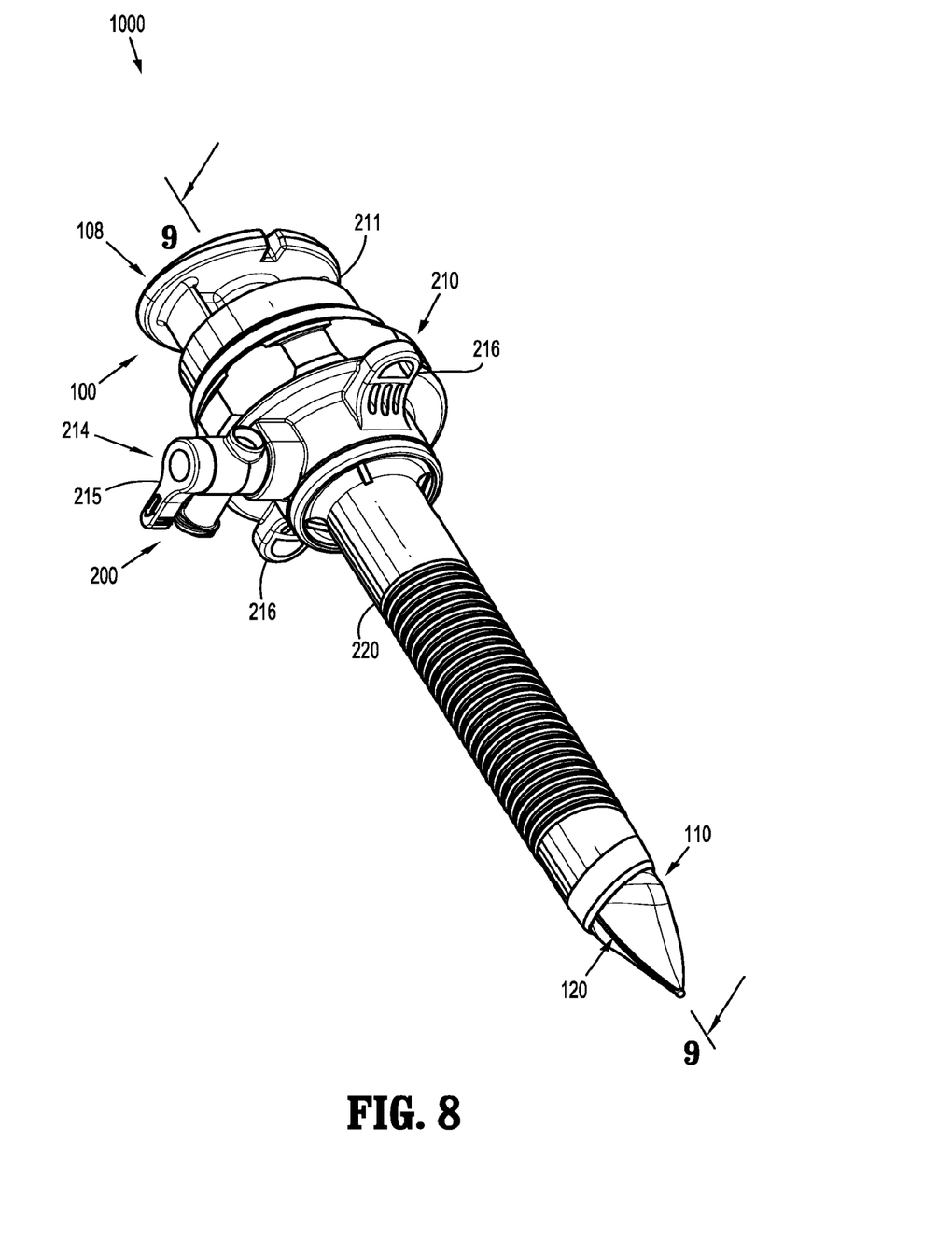
FIG. 8 is a perspective view of a surgical access apparatus according to the present disclosure, including the obturator of FIG. 1.

Referring initially to FIG. 8, a surgical access apparatus 1000 is shown. Surgical access apparatus 1000 includes an obturator 100 insertable through a cannula 200, which will be described further in detail below.

Figure 1:
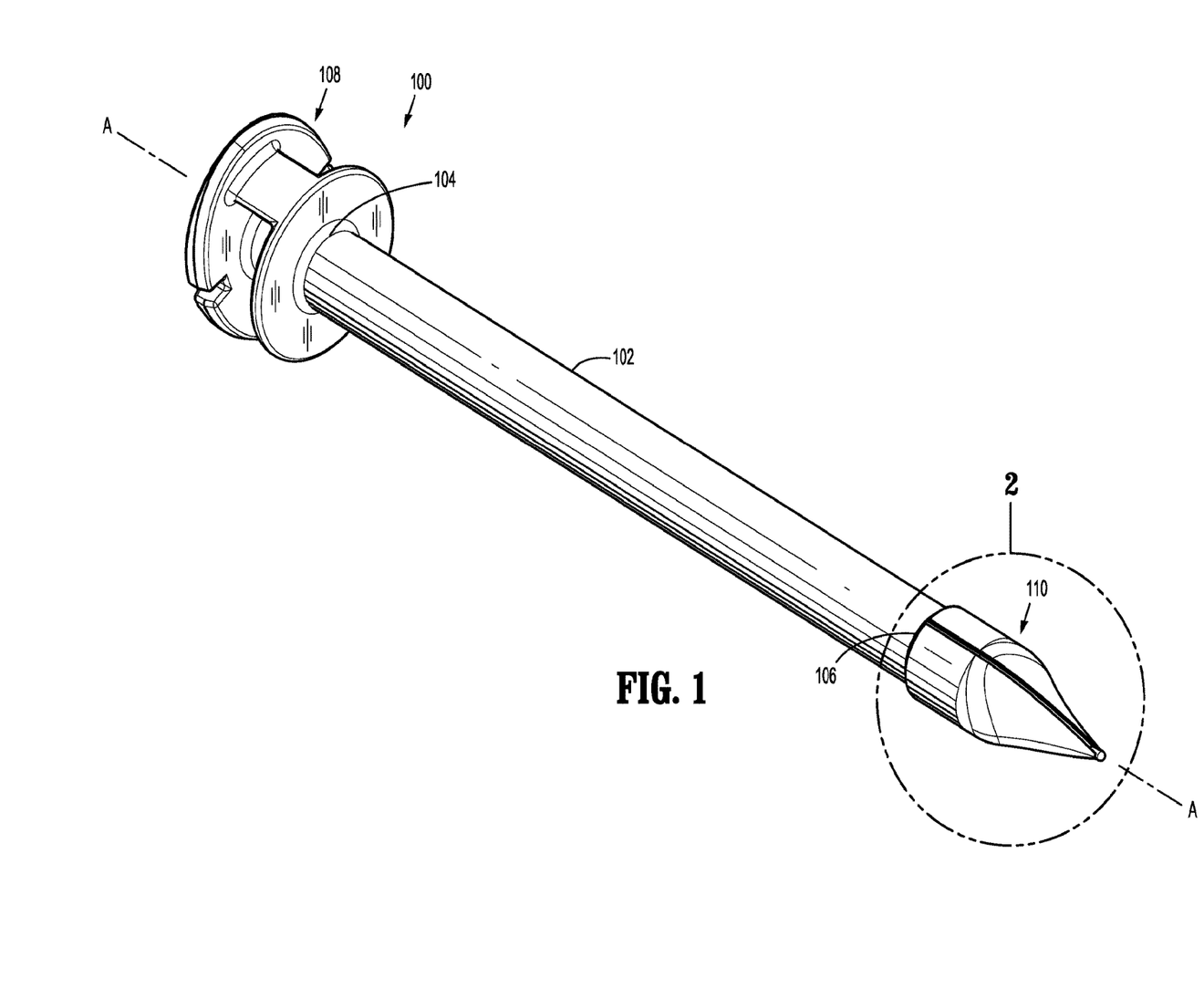
FIG. 1 is a perspective view of an obturator including a tip member in accordance with the present disclosure.

Referring now to FIG. 1, obturator 100 includes an obturator shaft 102, a tip member 110, and a handle 108. Obturator shaft 102 is an elongate member that defines a longitudinal axis "A", and has a proximal end 104 and a distal end 106. A handle 108 is mounted to the proximal end 104 of obturator shaft 102 and may include surface features suitable for grasping by an operator, e.g., an ergonomic grip incorporating flanges, curves, knurls, or the like.

Figure 2:
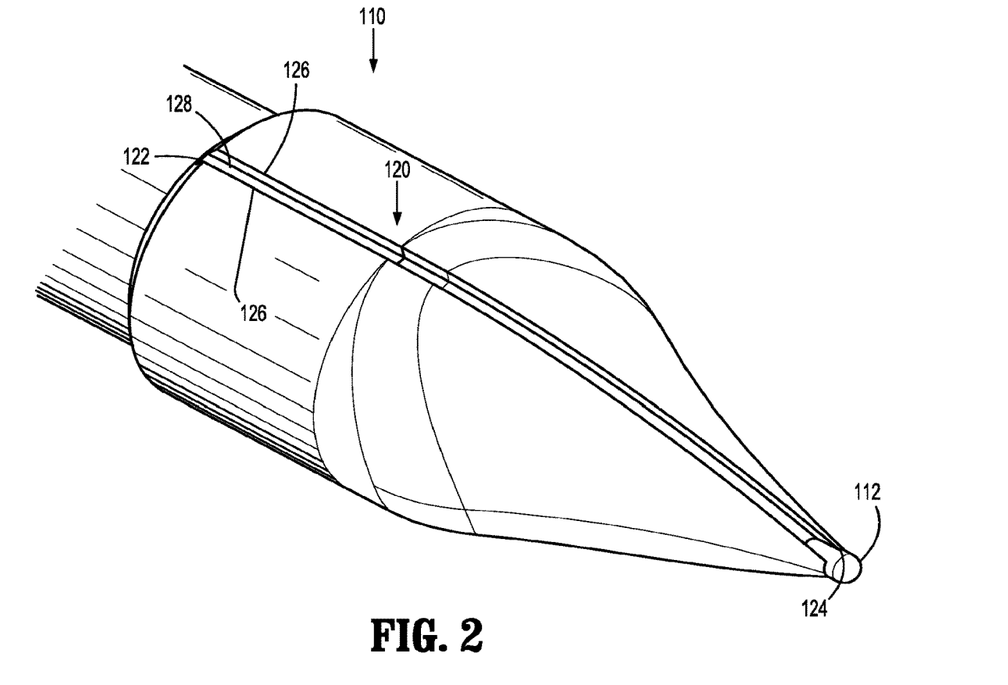
FIG. 2 is an enlarged view of the area of detail identified in FIG. 1.

Turning to FIG. 2, tip member 110, as shown, may have a tapered, e.g., conical, pyramidal, curved, etc., configuration that tapers to a distal tip 112. Distal tip 112 may be blunt, as shown, or may have another desirable atraumatic configuration, e.g., curvate, spheroid, or flat. In other embodiments, distal tip 112 may be sharpened or pointed so as to be configured to penetrate tissue.

A channel 120 may be formed on an outer surface of the tip member 110. Channel 120, as shown, is contoured to the outer surface of tip member 110 and extends along the length of tip member 110. Channel 120 includes an open proximal end 122 opposite an open distal end 124. Distal end 124 may be coterminous with distal tip 112, or distal tip 112 may protrude past the distal end 124 of channel 120, as shown. Channel 120 is defined by a pair of opposed walls 126 joined by a channel floor 128. Channel 120 may have any desirable configuration, e.g., arcuate or U-shaped, or may be configured as a closed member extending along the tip member 110, e.g., a tube or box when viewed in cross-section. Channel 120 defines a path through which fluids, e.g., insufflation fluids, may flow. In further embodiments, the walls 126 or channel floor 128 may incorporate surface features such as grooves or curves, e.g., to direct or alter fluid flow through channel 120. Tip member 110 may include any number or configuration of channels 120.

In some instances, the outer diameter of the obturator 100 may closely match the inner diameter of cannula 200. Thus, in some embodiments, channel 120 may extend along the entire length of obturator 100 or substantially the entire length of obturator 100. The channel 120 may be fluidly coupled directly to insufflation port 214 (FIG. 8).

Channel 120 may be formed on an outer surface of tip member 110 by, e.g., cutting, etching, laser treatment, electrical arcing, and the like. In embodiments, tip member 110 may be molded in a die or template such that channel 120 is pre-formed. Those skilled in the art of the present disclosure will envision other suitable methods of forming channel 120.

Figure 3:
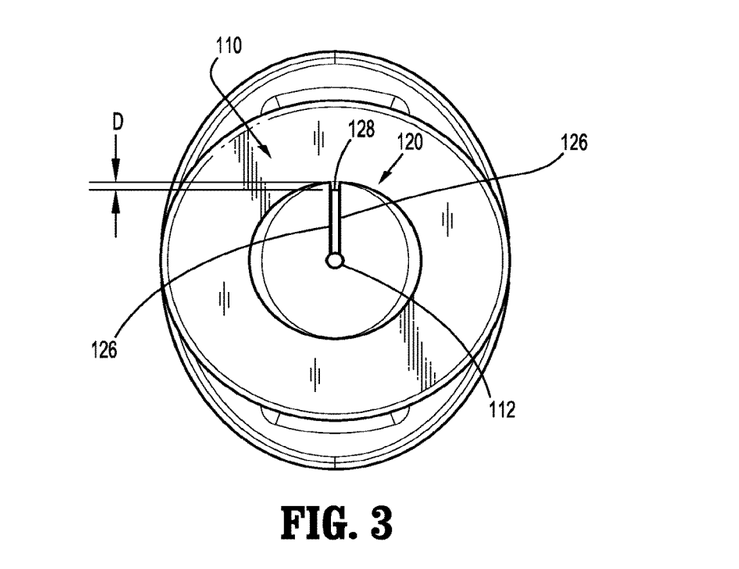
FIG. 3 is a bottom plan view of the obturator shown in FIG. 1.

Referring additionally to FIG. 3, channel 120, as shown, extends radially inward at a depth "D" along the outer surface of the tip member 110. Depth D, as shown, may be a constant dimension measured radially inward from an outer surface of the tip member 110. In this manner, channel floor 128 is disposed a depth D from the outer surface of tip member 110 as the channel 120 extends along the tapered profile of the tip member 110 toward the distal tip 112. In embodiments, the depth D of channel 120 may vary along the longitudinal length of the tip member 110, e.g., the distance between the outer surface of the tip member 110 and the channel floor 128 may increase or decrease along the longitudinal length of tip member 110.

Figure 4:
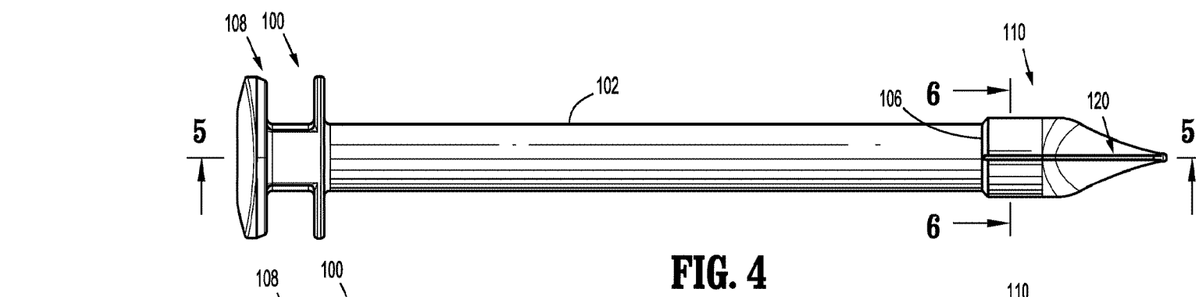
FIG. 4 is a side view of the obturator shown in FIG. 1.
Figure 5:
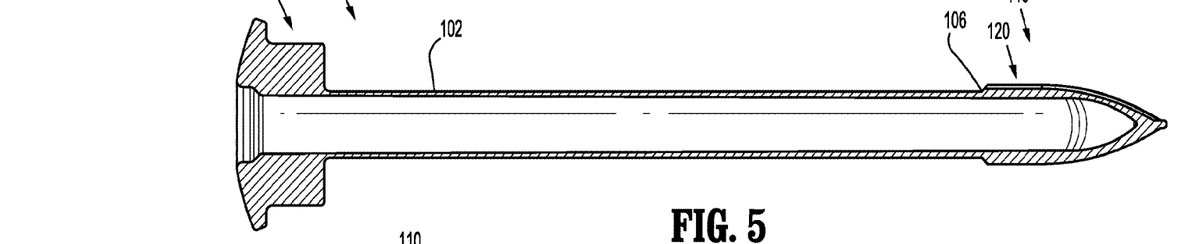
FIG. 5 is a cross-sectional view taken along section line 5-5 of FIG. 4.

Referring now to FIGS. 4 and 5, tip member 110 is shown coupled with obturator shaft 102. Tip member 110 may be mounted to the distal end 106 of obturator shaft 102 by any suitable means, e.g., press-fit, threaded connection, bayonet-type coupling, adhesion, or ultrasonic welding. In embodiments, tip member 110 and obturator shaft 102 may be integrally formed. Additionally, tip member 110 may be overmolded about a pre-existing tip member, or one or more channels 120 may be formed on a pre-existing tip member in the manner described above. Accordingly, tip member 110 may be configured and dimensioned to be retrofitted to a number of existing devices and obturators.

Figure 6:
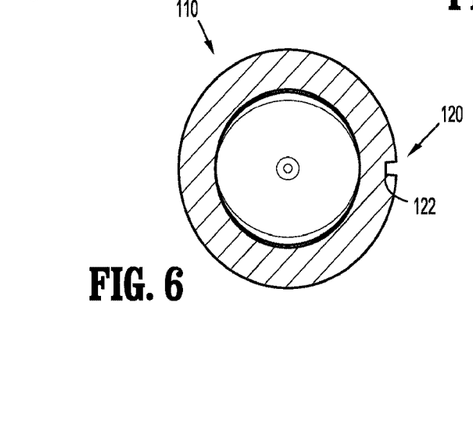
FIG. 6 is a cross-sectional view taken along section line 6-6 of FIG. 4.
Figure 7:
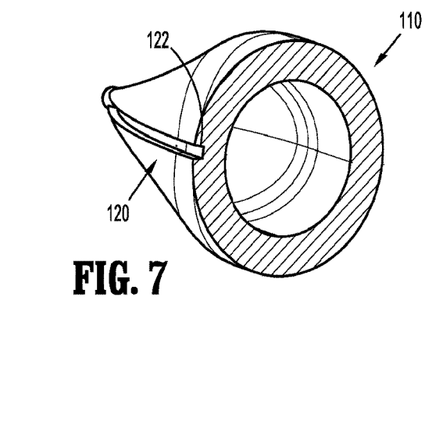
FIG. 7 is a perspective view of the cross-section taken along section line 6-6 of FIG. 5.

Referring additionally to FIGS. 6 and 7, the open proximal end 122 of channel 120 provides an entrance path to channel 120 as a fluid, e.g., insufflation fluid, advances distally along the obturator shaft 102 toward the tip member 110. Tip member 110, as shown, may have a hollow interior, or may be a solid member. In embodiments, tip member 110 may incorporate a transparent region or optical window through which light may pass, allowing for visualization or illumination outside the tip member 110 with an endoscope or other viewing device (not shown).

Figure 9:
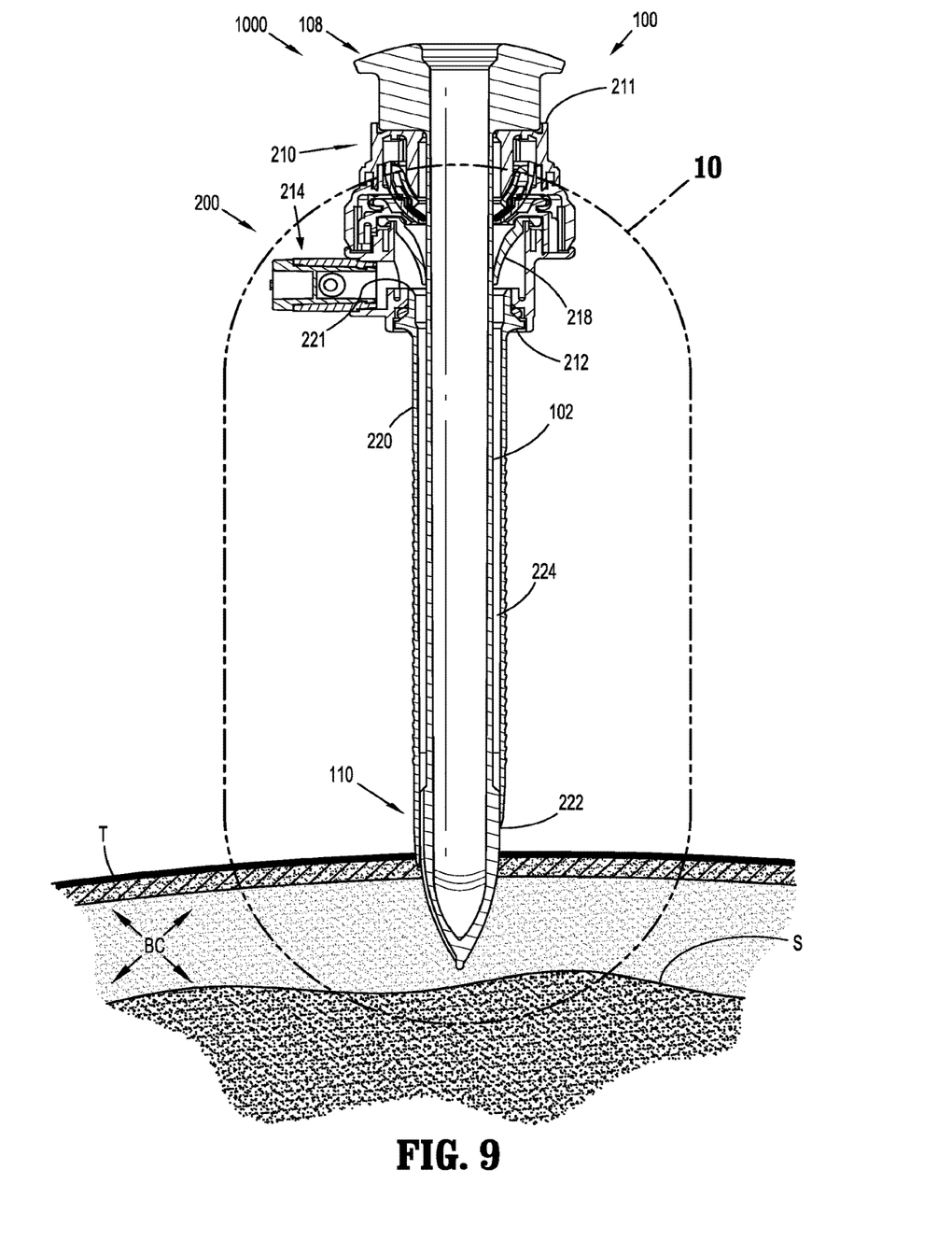
FIG. 9 is a cross-sectional view taken along section line 9-9 of FIG. 8, shown together with a cross-section of a layer of tissue and underlying body cavity.

Turning now to FIGS. 8 and 9, the obturator 100 is configured for insertion through cannula 200. Cannula 200 includes a housing 210 and a cannula shaft 220 extending distally from the housing 210. Housing 210 defines an interior annular recess and includes a proximal end 211 and a distal end 212 each defining an aperture configured to accommodate insertion of the obturator shaft 102 therethrough. Cannula shaft 220 has an open proximal end 221 opposite an open distal end 222, and defines an internal lumen 224 extending from the proximal end 221 to the distal end 222. Lumen 224 is dimensioned to accommodate passage of the obturator shaft 102 and tip member 110 through the cannula shaft 220.

A seal member 218, as shown, may be disposed within housing 210. Seal member 218 may be press fit, adhered, welded, or otherwise secured within housing 210. Seal member 218 is configured to sealably engage obturator shaft 102, or an instrument inserted therethrough. Accordingly, seal member 218 may be configured as a septum, conical, or disc seal. In embodiments, seal member 218 may be configured as a zero-closure seal, e.g., a duckbill, and may be configured to inhibit the proximal migration of fluids through cannula 200 in the absence of an instrument inserted therethrough. In further embodiments, cannula 200 may incorporate multiple seal members of varying configurations. Such seal members may be disposed in either or both the cannula housing 210 or cannula shaft 220.

Obturator 100, as shown, is insertable through lumen 224 of cannula shaft 220. Obturator 100 is dimensioned such that upon engagement of the handle 108 with the proximal end 211 of housing 210 of cannula 200, a portion of tip member 110 and channel 120 is exposed distally of the cannula shaft 220. At least a portion of tip member 110 remains disposed within lumen 224, as will be described further below.

Housing 210, as shown, includes an insufflation port 214 for transmitting fluids, e.g., insufflation fluids, therethrough. Insufflation port 214 may be configured as a stopcock or other suitable fluid port. Insufflation port 214 may be coupled with, e.g., a source of insufflation fluid or vacuum, or to a fluid line connected to a fluid source. Insufflation port 214 may include a valve 215 or fluid lock for selectively controlling the flow of fluids through insufflation port 214.

A pair of tabs 216 extends radially outward from an outer surface of the housing 210. Tabs 216 are suitable for grasping by an operator, e.g., the ring and index finger of one hand. Thus, tabs 216 provide an ergonomic grip such that an operator may grasp tabs 216 together with the handle 108 of obturator 100 to facilitate translation of the obturator 100 relative to the cannula 200. In this manner, an operator may also move the entire surgical access apparatus 1000.

With continued reference to FIG. 9, the surgical access apparatus 1000, as shown, is configured to be inserted through a layer of tissue "T". Tissue T defines a body cavity "BC", which may include underlying structures "S", such as tissue or body organs.

Figure 10:
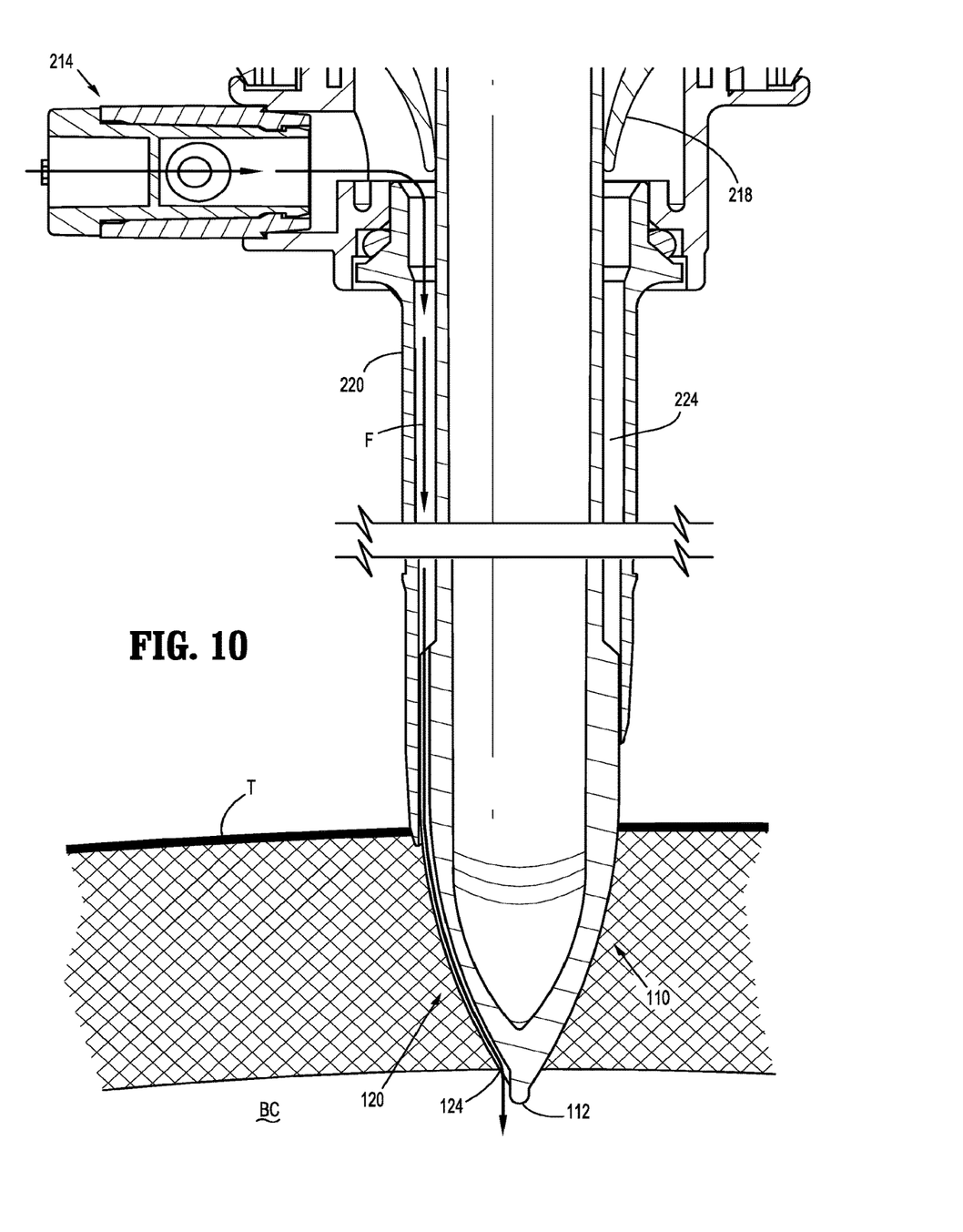
FIG. 10 is an enlarged view of the area of detail identified in FIG. 9.

FIG. 10 illustrates an initial penetration or incision of tissue T. An operator may grasp handle 108 of obturator 100 and tabs 216 of cannula 200 (FIG. 8), and, upon distal movement of obturator 100, tip member 110 dilates and advances through tissue T, creating a path for cannula shaft 220 to be inserted through tissue T. Cannula shaft 220 may include one or more visual indicator(s) to indicate the position of cannula 200 within the tissue. For instance, the visual indicator(s) may inform a user as to when the entire distal end 222 is within the incision. Thus, the user would know that surgical access apparatus 1000 is in a position where insufflation gas would be effectively trapped by the tissue and retained within the insufflation channel 120.

Insufflation fluids "F" are introduced through insufflation port 214 and into lumen 224 of cannula shaft 220. The presence of the obturator shaft 102 within lumen 224 defines an annular space through which insufflation fluids F flow. Seal member 218, as described above, inhibits the proximal migration of insufflation fluids F through the cannula shaft 220. Accordingly, pressurized insufflation fluids F entering cannula 200 through insufflation port 214 advance distally through lumen 224 toward tip member 110.

A proximal portion of channel 120, as shown, is disposed within and in fluid communication with lumen 224. With additional reference to FIG. 7, the proximal end 122 of channel 120 is exposed within the lumen 224 such that insufflation fluids F may enter channel 120 and advance distally into body cavity BC. As pressurized fluids F build up within lumen 224, channel 120 provides a path of least resistance along which pressurized insufflation fluids F will escape the higher-pressure environment within lumen 224. Accordingly, controlling the rate of flow through insufflation port 214 affects the fluid pressure within lumen 224 and the subsequent flow of insufflation fluids F along channel 120 and into body cavity BC.

In this manner, the supply of insufflation fluids F to body cavity BC is achieved directly through the cannula 200. The passage of insufflation fluids F along an outer surface of the tip member 110 of obturator 100 obviates the need for an additional insufflation supply and accompanying sealing structure for obturator 100, as will described in further detail below.

Figure 11:
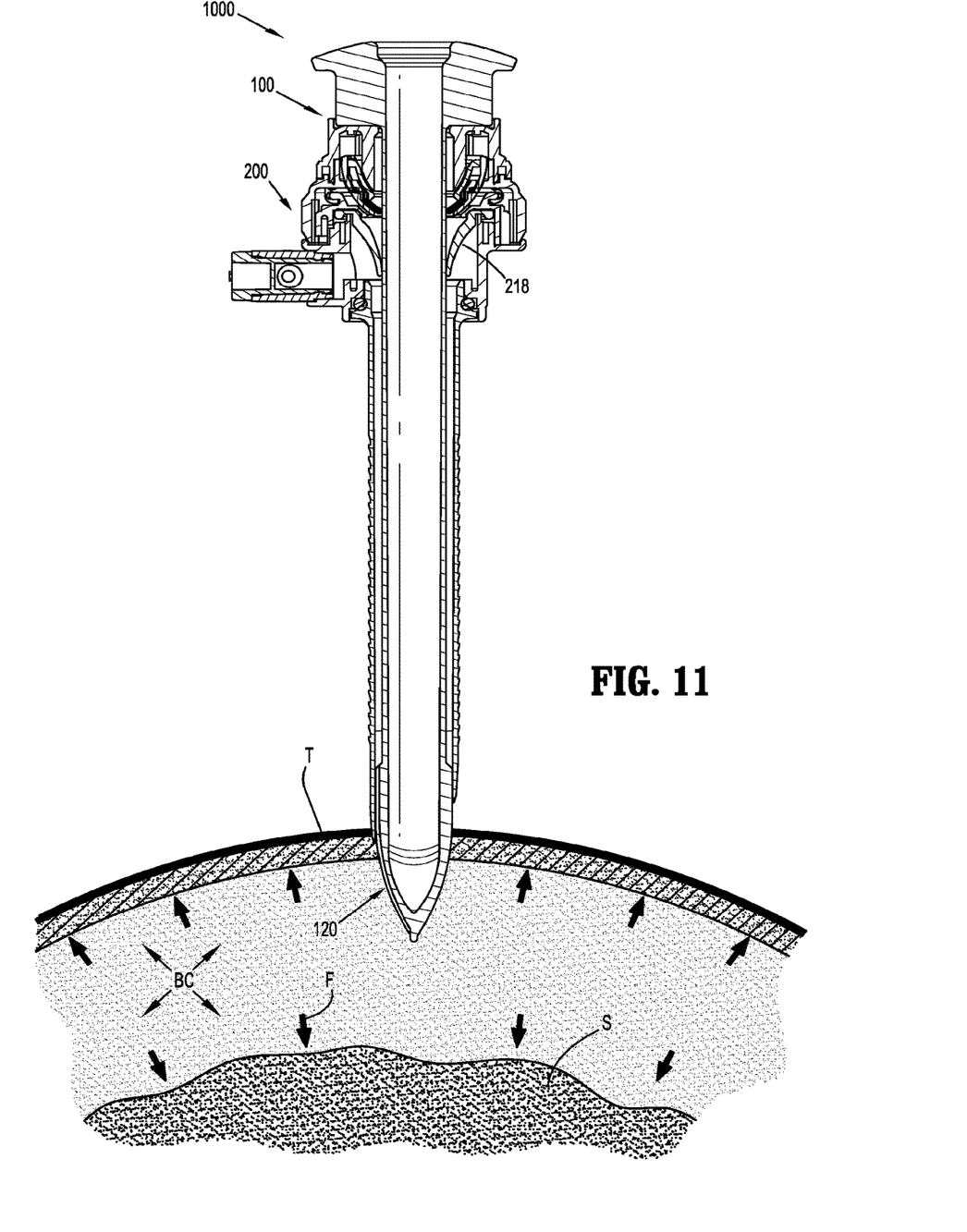
FIG. 11 is a cross-sectional view taken along section line 9-9 of FIG. 8, shown together with a cross-section of a layer of tissue and underlying insufflated body cavity.

The introduction of pressurized insufflation fluids F into body cavity BC creates an insufflated workspace such that tissue T may be lifted away from underlying structures S (FIG. 9). As shown in FIG. 10, the positioning of the distal end 124 of the channel 120 at or near the distal end of the tip member 110 enables insufflation fluids to begin to be introduced into the body cavity almost immediately upon the distal tip of the tip member penetrating through the abdominal wall. Accordingly, a larger working space is created for a minimally invasive procedure such that further advancement of the obturator 100 safely into body cavity BC is possible, facilitating, e.g., visualization or illumination of the body cavity BC, or further dilation of tissue T or structures S to reach a desired working site. Once the tissue, e.g, the abdominal wall, has been fully penetrated (see, e.g., FIG. 11), the obturator 100 may be withdrawn from the cannula 200, and another instrument (not shown) may be inserted through the cannula 200. As described above, the seal member 218 may be configured to maintain insufflation fluids F within body cavity BC in the absence of obturator 100 or another instrument.

Figure 12:
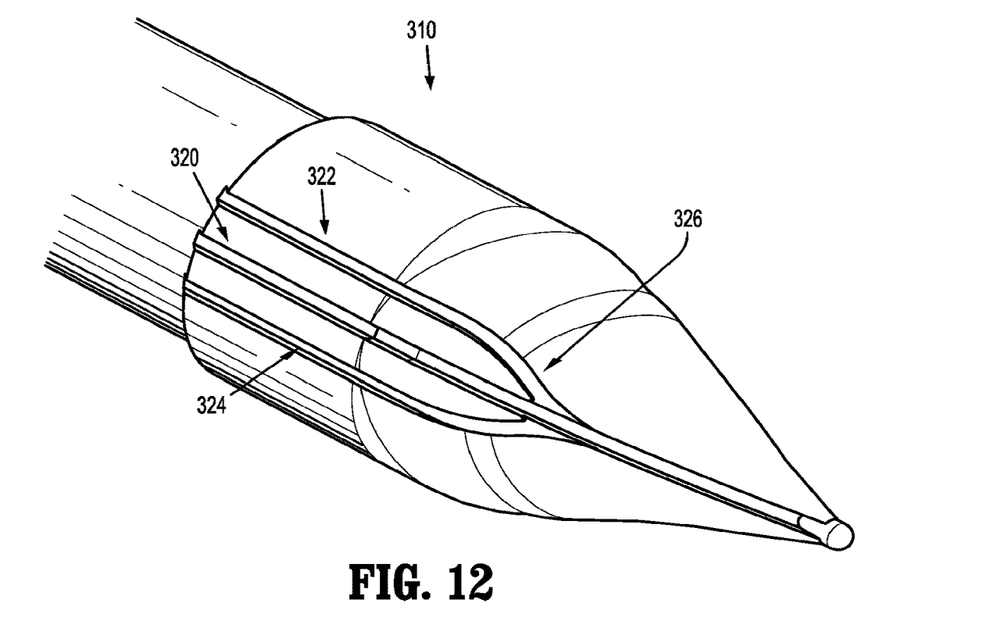
FIG. 12 is an enlarged perspective view of a tip member according to an alternative embodiment of the present disclosure.

Turning now to FIG. 12, an alternative embodiment of a tip member according to the present disclosure, designated tip member 310, is shown. Tip member 310 includes a channel 320 that is substantially similar to channel 120 described above. Each of side channels 322, 324 includes a proximal portion in parallel relation with channel 320, and a distal portion that curves toward and merges with channel 320 at an intersection 326 along the surface of tip member 310. Channel 320 and side channels 322, 324 are in fluid communication such that insufflation fluids F (FIG. 9) entering any of channel 320 or side channels 322, 324 will reach a distal portion of channel 320 at intersection 326. Accordingly, insufflation fluids F may be supplied to a distal portion of channel 320 through any of side channels 322, 324, or directly through a proximal portion of channel 320 to reach a body cavity BC (FIG. 9). In this manner, several paths are provided for insufflation fluids F to exit lumen 224 (FIG. 9) and reach body cavity BC such that an obstruction of one path does not inhibit the insufflation of body cavity BC. In further embodiments, tip member 310 may include any number or configuration of side channels.

Figure 13:
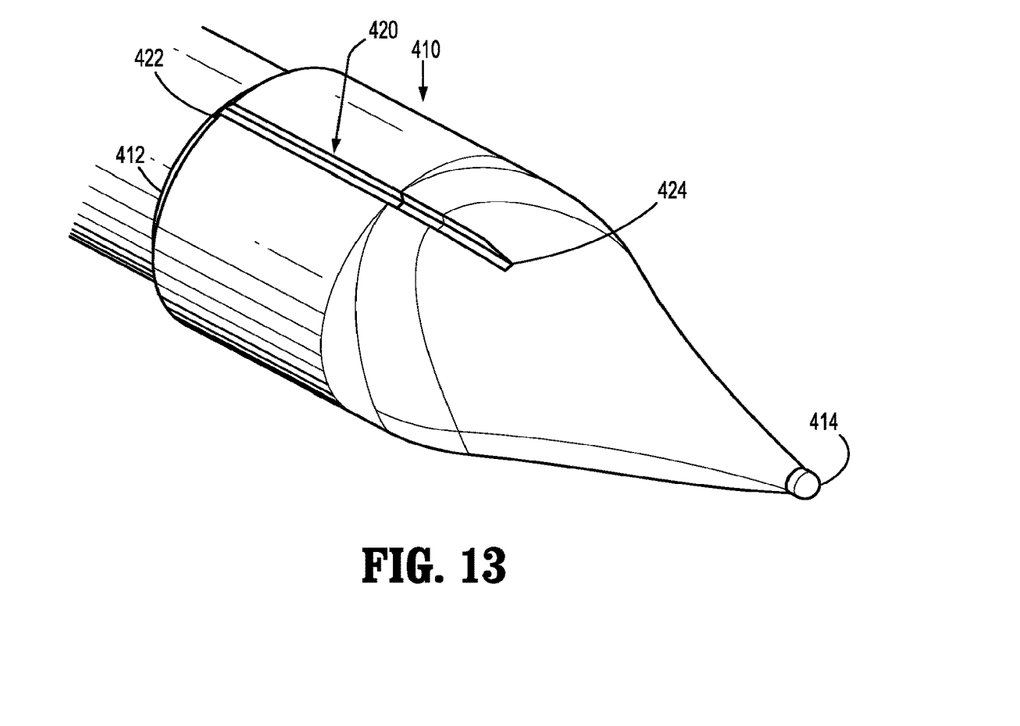
FIG. 13 is an enlarged perspective view of a tip member according to another alternative embodiment of the present disclosure.

Turning now to FIG. 13, a further embodiment of a tip member according to the present disclosure, designated 410, is shown. Tip member 410 includes a proximal end 412 and a distal end defined by a distal tip 414. A channel 420 is formed on an outer surface of the tip member 410, and has a similar configuration to channel 120 described above. Channel 420 includes an open proximal end 422 coincident with the proximal end 412 of tip member 410, and an open distal end 424. Channel 420 extends a portion of the longitudinal length of tip member 410 such that the open distal end 424 of channel 420 is spaced proximally away from the distal tip 414 of tip member 410. Accordingly, the path defined by channel 420 is contoured about a portion of the outer surface of tip member 410, and insufflation fluids F (FIG. 9) advancing through channel 420 exit the open distal end 424 of channel 420 at a distance longitudinally and radially spaced away from the distal tip 414. In this manner, the flow profile of insufflation fluids F may be controlled, e.g., to reach outlying structures S (FIG. 9) or to disperse insufflation fluids F over a wider area.

The present invention may provide various advantages over conventional arrangements, such as the use of a veress needle to introduce insufflation fluids. As shown in FIG. 10, the positioning of the distal end 124 of the channel 120 at or near the distal end of the tip member 110 enables insufflation fluids to begin to be introduced into the body cavity almost immediately upon the distal tip 112 of the tip member 110 penetrating through the abdominal wall. By eliminating the use of a veress needle, this arrangement minimizes the likelihood that an injury to underlying anatomical structures will occur. The introduction of pressurized insufflation fluids F into body cavity BC in order to create an insufflated workspace (which is typically a requirement of laparoscopic surgeries such that tissue T may be lifted away from underlying structures S) is performed much more safely than with a conventional veress needle.

Still further, the present invention may provide various advantages over conventional arrangements such as certain optical obturators. For example, there exist optical obturators that receive endoscopes therein; these optical obturators may include holes along their shafts or at their proximal ends for allowing insufflation fluid to enter the hollow interior of the optical obturator, as well as holes near the distal end thereof for expelling the insufflation fluids from the hollow interior and into a body cavity. While these distally located holes may provide for the flow of insufflation fluids, they are located more proximally relative to its respective distal most tip than may be achieved by the positioning of the distal end 124 of the channel 120, and thus the distal most tip of these conventional optical obturators must be inserted farther into a body cavity in order for insufflation fluids to begin to flow into the body cavity. By needing to be inserted farther into a body cavity prior to insufflation fluids beginning to flow into the body cavity, these conventional optical obturators have a higher risk of inadvertently damaging the underlying anatomical structures.

In contrast, in various embodiments of the present invention, the distal end 124 of the channel 120 may be positioned at the distal most end of the tip member 110. This arrangement enables insufflation fluids to begin to be introduced into the body cavity almost immediately upon the distal tip of the tip member penetrating through the abdominal wall, and earlier than would be possible in such above-described conventional optical obturators. This further reduces the likelihood that an injury to underlying anatomical structures will occur and further improves patient safety.

An additional advantage of the present invention as compared to above-described conventional optical obturators is that the provision of channels on the outer surface of the tip member may help avoid problems that are caused by the arrangements of the conventional optical obturators, e.g., that have holes that are in fluid communication with the hollow interior of the obturator. The above-described conventional optical obturators receive endoscopes in their hollow interiors, and thus having holes in the obturator walls as they do requires that a seal be provided in the interior of the obturator, e.g., at the proximal end thereof, in order to prevent the proximal flow and escape of insufflation gas between the interior wall of the obturator and the outer surface of the endoscope. This seal adds costs and complexity to the manufacture of this conventional optical obturator, as well as provides another potential leak path during a surgical procedure.

In contrast, the provision of channels on the outer surface of the tip member, as described hereinabove in connection with the present invention, avoids the need for a seal in the interior of the obturator. Since the channels are not in fluid communication with the hollow interior of the obturator, insufflation fluids that enter into the annular space within the cannula do not enter the interior of the obturator, and thus there is no possibility that the insufflation fluids will flow proximally and escape between the interior wall of the obturator and the outer surface of the endoscope. Rather, insufflation fluids flow only through the channel 120 and into the body cavity, and an endoscope that is inserted within the optical obturator need not be sealed relative thereto.

A still further advantage of the present invention as compared to the above described conventional optical obturators is that the provision of channels on the outer surface of the tip member may help avoid the need for other seals that are employed in the above-described conventional optical obturators. For example, these conventional optical obturators may also include a seal at the distal end of the cannula tube, this distal cannula seal sealing between the cannula tube and the outer surface of the obturator. Such a seal is typically necessary such that insufflation gas received via the cannula housing is directed first through the holes in the optical obturator and into the interior of the optical obturator and then out of the interior through the distal most hole of the obturator. Without the distal cannula seal, insufflation gas received via the cannula housing would attempt to be expelled out of the distal end of the cannula tube, between the inner wall of the cannula tube and the outer surface of the obturator, but would be prevented from doing so because of the direct contact between the tip of the optical member and the tissue. Again, this distal cannula seal adds costs and complexity to the manufacture of this conventional optical obturator, as well as provides another potential leak path during a surgical procedure.

In contrast, the provision of channels on the outer surface of the tip member, as described hereinabove in connection with the present invention, avoids the need for this distal cannula seal. In various embodiments of the present invention, insufflation gas received via the cannula housing is expelled out of the distal end of the cannula tube, between the inner wall of the cannula tube and the outer surface of the obturator. However, instead of being prevented from being expelled because of the direct contact between the tip of the optical member and the tissue (as is the case with the above-described conventional optical obturators), the provision of the channel or channels on the outer surface of the tip member provide a path for such insufflation gas to flow, and specifically a path to the distalmost tip of the tip member so as to be expelled into a body cavity immediately as the wall of the body cavity is penetrated.

The present invention, according to various embodiments thereof, may also provide the advantage that it requires virtually no modifications of the various components of a trocar. As set forth above, not only must the above-described conventional optical obturators provide two additional seals (a first seal between the interior surface of the optical obturator and the endoscope; and a distal cannula seal between the interior surface of the cannula tube and the outer surface of the optical obturator), but almost all of the components of this system are required to be re-designed as compared to an ordinary trocar in order to accommodate these seals and the desired flow of insufflation gas into the interior of the optical obturator. In contrast, every component of the system of the present invention save the tip member, may—if desired—remain completely unchanged from an ordinary trocar, thereby saving costs and enabling the advantages of the present invention to be provided simply by providing a channeled tip member on an ordinary trocar system, without requiring modification of the remaining components of the trocar system.

It will be understood that various modifications may be made to the embodiments disclosed herein. Therefore, the above description should not be construed as limiting, but merely as exemplifications of embodiments. Those skilled in the art will envision other modifications within the scope and spirit of the present disclosure.

The invention claimed is:

1. A surgical access apparatus, comprising:
    a cannula defining an internal lumen; and
    an obturator insertable through the internal lumen of the cannula, the obturator including:
        an obturator shaft having a proximal end and a distal end, and defining a first diameter; and
        a tip member at the distal end of the obturator shaft, the tip member having a cylindrical portion defining a second diameter, wherein the second diameter is greater than the first diameter, the tip member having an outer surface, the outer surface defining a linear channel adapted for conducting fluid, wherein the linear channel extends from a proximal end of the tip member to a distal most point of the tip member, wherein a flow path is defined between the proximal end of the obturator shaft and the distal most point of the tip member.

2. The surgical access apparatus of claim 1, wherein the obturator is configured to receive an endoscope.

3. The surgical access apparatus of claim 1, wherein at least a portion of the tip member is transparent.

4. The surgical access apparatus of claim 1, wherein the linear channel defines a first fluid path that is separate from an interior of the obturator.

5. The surgical access apparatus of claim 1, wherein the outer surface of the tip member includes a plurality of linear channels.

6. The surgical access apparatus of claim 1, wherein an interstitial space is defined between an outer surface of the obturator shaft and an inner surface of the internal lumen of the cannula.

7. The surgical access apparatus of claim 6, wherein a portion of the linear channel is in fluid communication with the interstitial space.

8. The surgical access apparatus of claim 1, wherein the cannula further includes a housing and a cannula shaft, the cannula shaft including an internal lumen.

9. The surgical access apparatus of claim 8, wherein the housing includes opposed proximal and distal apertures.

10. The surgical access apparatus of claim 9, wherein the obturator is insertable through the internal lumen such that at least a portion of the linear channel extends beyond the distal aperture.

11. The surgical access apparatus of claim 1, wherein at least one seal member is disposed in the cannula, and is configured to form a fluid-tight seal with the obturator shaft inserted therethrough.

12. The surgical access apparatus of claim 1, wherein the cannula is configured to be coupled to a source of fluid.

13. The surgical access apparatus of claim 1, wherein the linear channel is defined by an open proximal end, an open distal end, and a pair of opposed walls extending therebetween.

14. An obturator configured to be inserted through a cannula, the obturator comprising:
    an obturator shaft having a tip member at a distal end of the obturator shaft, the obturator shaft defining a first diameter and the tip member including a cylindrical portion defining a second diameter, the second diameter is greater than the first diameter, the tip member having an outer surface that defines a U-shaped linear channel configured to convey fluid from a proximal end of the tip member to a distal most point of the tip member.

15. The obturator of claim 14, wherein the obturator shaft has a hollow interior.

16. The obturator of claim 14, wherein the hollow interior of the obturator shaft is configured to receive an endoscope.

17. The obturator of claim 14, wherein at least a portion of the tip member is transparent.

* * * * *